United States Patent [19]

Tedder

[11] Patent Number: 4,692,432
[45] Date of Patent: Sep. 8, 1987

[54] TWO CYCLE PROCESS FOR PRODUCING FUEL-GRADE ETHANOL FROM DILUTE AQUEOUS MIXTURES

[75] Inventor: Daniel W. Tedder, Marietta, Ga.

[73] Assignee: Georgia Tech Research Corporation, Atlanta, Ga.

[21] Appl. No.: 764,390

[22] Filed: Aug. 12, 1985

Related U.S. Application Data

[63] Continuation-in-part of Ser. No. 534,262, Sep. 21, 1983, Pat. No. 4,517,298, which is a continuation of Ser. No. 265,328, May 18, 1981, abandoned, and a continuation-in-part of Ser. No. 544,813, Oct. 10, 1983, Pat. No. 4,510,242, which is a continuation of Ser. No. 283,739, Jul. 15, 1981, abandoned.

[51] Int. Cl.$^4$ .................... C07C 29/86; C07C 31/08
[52] U.S. Cl. ............................... 568/916; 44/56; 548/918
[58] Field of Search ....................... 568/918, 916

[56] References Cited

U.S. PATENT DOCUMENTS

| | | | |
|---|---|---|---|
| 2,597,009 | 5/1952 | Lobo et al. | 568/916 |
| 3,455,664 | 7/1969 | Rosscup et al. | 568/918 |
| 3,793,379 | 2/1974 | Rosscup et al. | 568/918 |
| 4,260,836 | 4/1981 | Levy | 568/918 |
| 4,306,884 | 12/1981 | Roth | 568/918 |
| 4,342,627 | 8/1982 | Cane et al. | 568/916 |
| 4,346,241 | 8/1982 | Feldman | 568/916 |
| 4,399,000 | 8/1983 | Tedder | 568/918 |
| 4,425,137 | 1/1984 | Roth | 568/918 |
| 4,510,242 | 4/1985 | Tedder | 568/918 |
| 4,517,298 | 5/1985 | Tedder | 435/160 |

FOREIGN PATENT DOCUMENTS

| | | | |
|---|---|---|---|
| 176919 | 10/1982 | Japan | 568/916 |
| 577201 | 10/1977 | U.S.S.R. | 568/918 |

OTHER PUBLICATIONS

Roddy, "Ind. Eng. Chem. Process Des. Dev.", vol. 20, No. 1, 1981, pp. 104–108.

Primary Examiner—J. E. Evans
Attorney, Agent, or Firm—Newton, Hopkins & Ormsby

[57] ABSTRACT

The beer is fed to a first solvent extraction column together with an organic solvent for alcohol which solvent is immiscible in water. The alcohol-organic solvent phase is extracted a second time, vacuum distilled or stripped, dried and again vacuum stripped or distilled to produce fuel grade alcohol.

17 Claims, 1 Drawing Figure

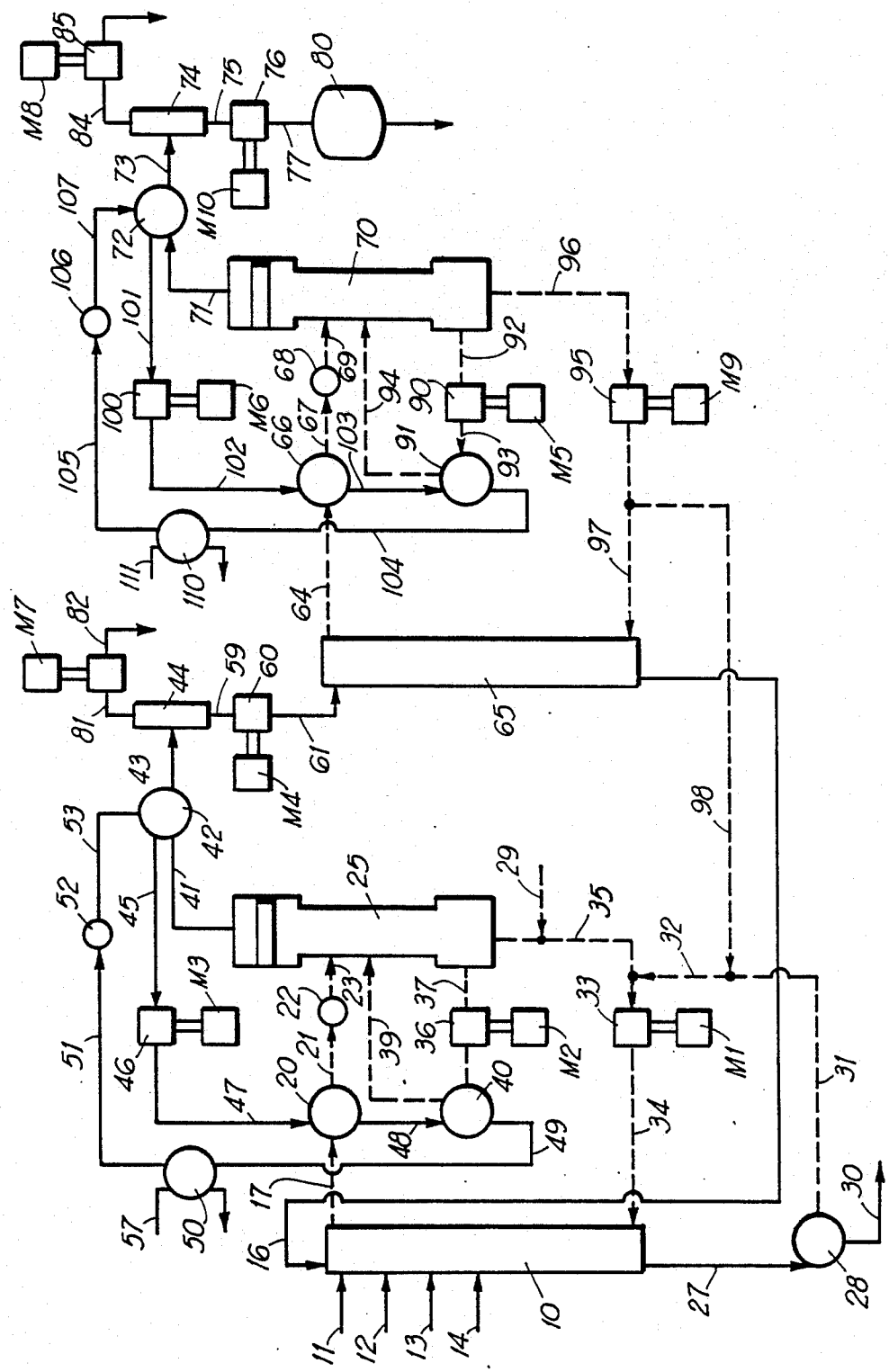

TWO CYCLE PROCESS FOR PRODUCING FUEL-GRADE ETHANOL FROM DILUTE AQUEOUS MIXTURES

CROSS REFERENCE TO RELATED APPLICATIONS

This application is a continuation-in-part of my copending application Ser. No. 534,262, filed Sept. 21, 1983, now U.S. Pat. No. 4,517,298, which was a continuation of my application Ser. No. 265,328, filed May 18, 1981, now abandoned, and a continuation-in-part of my application Ser. No. 544,813, filed Oct. 10, 1983, now U.S. Pat. No. 4,510,242, which was a continuation of Ser. No. 283,739, filed July 15, 1981, now abandoned.

BACKGROUND OF THE INVENTION

1. Field of the Invention

This invention relates to a process of producing alcohol and is more particularly concerned with a two cycle process for producing fuel grade alcohol from dilute aqueous mixtures.

2. Description of the Prior Art

In the past, fuel grade alcohol has been produced using conventional techniques for distilling the alcohol below the azeotrope. This alcohol is then dried using, for example, a benzene drying still to produce the fuel grade alcohol suitable for gasohol and other uses. In my U.S. Pat. No. 4,399,400, I have disclosed a process for producing fuel grade alcohol, using an organic solvent system to extract the alcohol into an organic solvent-alcohol phase. This phase is then vacuum distilled to recover the fuel grade alcohol. The patents cited in my patent are pertinent.

SUMMARY OF THE INVENTION

Briefly described, the present invention includes producing, through conventional fermentation, beer containing about 2 to about 4% alcohol (ethanol) in an aqueous mixture. Passing this beer to a solvent extraction cascade column. Feeding to the solvent extraction column, an organic solvent for removing the alcohol from the water. Removing the organic solvent alcohol extract (containing about 5% to about 10% alcohol) from the column and feeding it to a vacuum stripper or distiller where the overhead which is recovered therefrom contains about 50% to about 80% alcohol and is fed to a drying column where it is partially extracted in a drying cycle so that the extract contains from about 60% to about 90% of the ethanol. This alcohol solvent extract is then fed to a second vacuum stripper or distiller where fuel grade alcohol is produced. The organic solvent is a branched aliphatic hydrocarbon, namely isoparaffinic materials or a long chain alcohol, or a long chain fatty alcohol or a long chain fatty acid.

An object of the present invention is to provide a process for producing a dry, fuel grade, alcohol.

Another object of the present invention is to provide a process for continuously producing a fuel grade alcohol which process is less heat intensive and cheaper than conventional processes.

Other objects, features and advantages will become apparent from the following description when considered with the accompanying drawing.

BRIEF DESCRIPTION OF THE DRAWING

The FIGURE shows a schematic diagram of the process of the present invention.

DESCRIPTION OF THE PREFERRED EMBODIMENT

Referring now in detail to the embodiment chosen for illustrating the present invention, numeral 10 in the drawing denotes a solvent extraction column to which is fed a dilute alcohol water mixture known as beer, produced conventionally from the fermentation of a biomass containing sugars, and/or starches or from the enzymatic hydrolysis of cellulose. It will be understood that the present process can employ beer containing methanol, ethanol, propanol, isopropanol or butanol, for example, to recover that particular alcohol from an aqueous mixture containing the alcohol.

The beer is fed through a plurality of lines or conduits 11, 12, 13 and 14 as individual streams to the solvent extraction column 10 and unextracted ethanol from the drying cycle is fed via line 16, as an overhead stream down through the column 10. Recovery solvent to added to unit 10 via line 34. In the solvent extraction column 10, the alcohol is extracted from the mixture as the mixture cascades through the column 10. Thus, the alcohol and organic solvent form one phase and the water of the beer another phase, the two phases being substantially immiscible with each other.

The alcohol-organic solvent phase is fed, via line 17 and heat exchanger 20 through line 21, valve 22 and line 23 to a vacuum stripper or evaporator 25. The heat exchanger 20 increases the temperature of the alcohol-organic solvent fed to evaporator 25.

The bottom raffinate from column 10, consisting of the water phase and entrained solvent passes, via line 27, to a centrifuge 28. The centrifuge 28 separates the entrained solvent from the water phase. The water raffinate is discharged from centrifuge 28 via line 30, while the solvent phase is returned via lines 31, 32, pump 33 and line 34 to the solvent extraction column 10. Also, the regenerated solvent from vacuum stripper 25 is directed via line 35 to pump 33, and, thence, via line 34, to the solvent extraction column 10. Make up solvent is supplied, via line 29, to line 32.

A circulating pump 36 connected to the vacuum stripper or evaporator 25, by suction line 37, receives the bottom from the stripper 25 and pumps this bottom through a second heat exchanger 40 in which it is heated so as to maintain the temperature with the stripper or evaporator 25. This bottom is reintroduced or returned, via line 39, into an intermediate portion of the vacuum stripper 25.

The overhead from vacuum stripper 25, i.e., the alcohol vapor extract passes via line 41, a third heat exchanger 42 and line 43 to a collector 44. Thus, the solvent extraction column 10 and the vacuum stripper 25 perform the first or recovery cycle of the process.

For cooling heat exchangers 20, 40 and 42, these heat exchangers are arranged in series in a closed refrigeration system in which a cooling liquid is circulated from heat exchanger 50, via line 51, valve 52, line 53, heat exchanger 42, line 45, pump 46, line 47, heat exchanger 20, line 48, heat exchanger 40, line 49, back to heat exchanger 50.

The heat exchanger 42 cools the overhead from vacuum stripper 25 sufficiently that when fed to the collector 44 a barometric leg, the alcohol and water condensate, at about 120° F., is pumped, via line 59, pump 60 and line 61 to a drying column 65 which extracts the alcohol from the remaining water, passing the drying cycle extract via line 64, heat exchanger 66, line 67, valve 68 and line 69 to a second vacuum stripper or evaporator 70 which operates at approximately 20° F. Water and unextracted ethanol from the drying cycle are returned via line 16 to the recovery cycle.

The stripper or evaporator 70 separates the fuel-grade alcohol from the organic solvent, passing the alcohol overhead, via line 71, heat exchanger 72 and line 73 to a barometric leg 74. The condensate of condenser 74, at about 105° F., is pumped via line 75, pump 76, line 77 to storage tank 80.

The drying column 65 and the stripper 70 perform the second or drying cycle of the process.

A partial vacuum is maintained on barometric condenser 44 through line 81 by exhaust pump 82 which discharges to the atmosphere. A partial vacuum is maintained on barometric condenser 74 through line 84 and exhaust pump 85, pump 85 also discharging to the atmosphere.

A circulating pump 90 circulates the bottom of the second vacuum stripper 70 through a heat exchanger 91, via lines 92, 93 and 94 so as to maintain the temperature in the stripper 70 at about 20° F.

The regenerated drying solvent from the second vacuum stripper 70 is pumped via line 96, pump 95 line 97 to the bottom of the drying column 69 and also via line 98 (a bleed) to line 31 for return to the bottom of the solvent extraction column 10.

A refrigerant or cooling liquid is circulated by pump 100, from heat exchanger 110, via line 105, valve 106, line 107, heat exchanger 72, lines 101 and line 102 to heat exchanger 66 and then from heat exchanger 66, via line 103 to heat exchanger 91. Thence, the liquid is fed, via line 104, back to heat exchanger 110.

Motors M1, M2, M3, M4, M5, M6, M7, M8, M9 and M10 respectively drive pumps 33, 36, 46, 60, 90, 100, 82, 85, 95 and 76.

In the operation of the apparatus described above, the beer or fermentation liquor which contains from about 2% to about 4% by weight, ethanol (or other alcohol), in an aqueous slurry or mixture containing the sludge is fed to the solvent extraction column 10, via lines 11, 12, 13 and 14.

The organic drying cycle solvent is a water immiscible organic hydrocarbon having an affinity for alcohol. Preferably a chain isoparaffinic hydrocarbon of the general formulae:

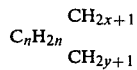

is used as the solvent, wherein n represents an integer from 4 to 9, x represents an integer from 4 to 9 and y represents an integer from 4 to 9. Such branch chain alkanes or isoparaffins solvents as Isopar-L, Isopar-M, Norpar-12 and Norpar-13 are suitable for this process with Isopar-L and/or Isopar-M being preferred. For a recovery cycle solvent, 5 to 100 volume % tridecy alcohol or tri-2-ethylhexyl phosphate may be added to the isoparaffin as a modifier to increase the ethanol solubility.

Long chain alcohol, such as tridecyl and decyl alcohol are suitable as modifiers for recovery solvent. Long chain fatty alcohols, incuding lauryl, cetearyl, cetyl, stearyl and tallow types are also suitable as organic modifiers and long chain esters such as coconut, tallow and linseed oil fractions are also useful as the organic solvent. Also, acetate esters of such species, such as tridecyl acetate, are good modifiers.

The beer typically contains from about 2% to about 4% alcohol and when this beer enters the solvent extraction column 10 the extract or overhead, through line 17, from the extraction column 10 is typically 5% to 10% alcohol (ethanol) depending on the recovery cycle operation. On the other hand, the intermediate product recovered from the recovery cycle, i.e., from the vacuum stripper 25 as fed through lines 41, 59 and 61 contains from about 50% to about 80% alcohol (ethanol). The extract product by the drying cycle, i.e., drying column 65, along line 64 contains from about 2 to about 5% alcohol (ethanol) and is fuel-grade (i.e. essentially water free).

In the process, the residual alcohol in the drying column 65 is not lost but is recycled to the recovery cycle (column 10) via line 16.

In the second vacuum stripper 70, the extract from the drying cycle, i.e., the dry alcohol (ethanol) is stripped, typically providing about 98% ethanol which is sufficiently dry to be fuel grade alcohol.

The advantages of this process are significantly reduced energy costs and the elimination of secondary waste production during the final drying step. Other techniques, require the addition of materials which lead to secondary wastes. For example, the use of drying agents ultimately results in secondary sludge wastes because it is difficult to regenerate the drying agents. The drying cycle of the present invention, on the other hand, recycles the solvent and does not generate secondary wastes. Solvent losses to the product only serve to increase the octane value of the fuel.

Standard equipment items may be used for liquid/liquid extraction and standard evaporators may be used for solvent stripping.

The two cycle concept of the present invention produces a synergistic effect between the recovery and drying cycles that makes this system more valuable than either of the cycles independently. Specifically, the recovery cycle makes high grade ethanol recovery possible. The drying cycle makes it possible to dry ethanol above the azeotrope without the addition of drying agents or other materials that produce secondary wastes. The drying cycle alone would not be attractive because it does not exhibit good ethanol recovery properties. The recovery cycle could be used alone to produce an intermediate ethanol/water mixture, but it would have a composition below the azeotrope.

It will be obvious to those skilled in the art that many variations may be made in the embodiment chosen for purpose of illustrating without departing from the scope thereof, as defined by the appended claims.

I claim:

1. A process of producing alcohol comprising feeding a dilute aqueous mixture containing said alcohol to a first solvent extraction column, feeding an organic solvent for said alcohol, which solvent is essentially immiscible with water, to said first extraction column for admixing with said aqueous mixture containing said alcohol, to dissolve the alcohol therefrom for forming an alcohol-organic solvent extract phase containing residual amounts of water, and a raffinate containing water and residual amounts of entrained solvent, alcohol and solids, separating said alcohol-organic solvent phase from said raffinate, vacuum stripping the water and alcohol from said extract phase, condensing the vacuum stripped water and alcohol and passing said alcohol-water to a second solvent extraction column serving as a drying column to obtain a second alcohol-organic solvent extract phase being relatively water free, separating the entrained solvent from said raffinate and returning said entrained solvent to said first solvent extraction column, passing the second alcohol-solvent extract phase from said second solvent extraction column to a vacuum stripper for separating the alcohol from the organic solvent and returning the organic solvent to said second solvent extraction column.

2. The process of claim 1 wherein said alcohol is ethanol.

3. The process defined in claim 1 wherein said organic solvent is selected from the group consisting of n-paraffin, isoparaffin, long chain alcohols, long chain fatty acids, and long-chain fatty acid esters or mixtures of such species.

4. The process defined in claim 1 wherein an overhead is formed in said first solvent extraction column and is fed to a vacuum stripper and a vacuum is applied thereto for again separating the alcohol-organic solvent phase from water therein, the again separated alcohol-organic solvent phase constituting the phase delivered to said drying column.

5. The process defined in claim 1 wherein said alcohol organic solvent is heated between said first solvent extraction column and said second solvent extraction column.

6. The process defined in claim 1 wherein an overhead containing alcohol is formed in the vacuum stripper and said alcohol from the overhead of said vacuum stripper is removed under a vacuum, cooled, and then pumped to strorage.

7. The process defined in claim 1 wherein the solids are separated from said raffinate, by centrifuging.

8. The process of claim 1 wherein a heat pump is interfaced between each solvent extraction and vacuum stripping to achieve energy reuse.

9. The process of claim 3 wherein said organic solvent is n-paraffin.

10. The process of claim 1 wherein said organic solvent for the first extraction column is a long chain alcohol selected from the group consisting of tridecyl alcohol and decyl alcohol, and said organic solvent for the second extraction column is isoparaffin.

11. A process for producing alcohol comprising feeding a dilute aqueous mixture containing said alcohol to a first solvent extraction column, feeding a first organic solvent for said alcohol, which first solvent is essentially immiscible with water, to said first extraction column for admixing with said aqueous mixture containing said alcohol, to dissolve the alcohol therefrom for forming a first alcohol-organic solvent extract phase containing residual amounts of water, and a first raffinate containing water and residual amounts of entrained first solvent, alcohol and solids, separating said first extract phase from said first raffinate, vacuum stripping the water and alcohol from said first extract phase, returning said first solvent to said first solvent extraction column, condensing the vacuum stripped water and alcohol to form a first condensate and passing said first condensate to a second solvent extraction column serving as a drying column to obtain a second alcohol-organic solvent extract phase being relatively water free, feeding a second organic solvent for said alcohol, which second solvent is essentially immiscible with water, to said second solvent extraction column for admixing with said first condensate to dissolve the alcohol therefrom for forming said second extract phase, using said second solvent extraction column to produce said second extract and a second alcohol-water raffinate phase, sending said second raffinate phase to said first extraction column for alcohol recovery, passing the second extract phase from said second solvent extraction column to a second vacuum stripper for separating the alcohol from said second organic solvent and returning said second organic solvent to said second solvent extraction column and producing a second dry alcohol condensate from alcohol vapors produced by said second vacuum stripper.

12. The process defined in claim 11 wherein an extract is formed in said first solvent extraction column and is fed to a first vacuum stripper and a vacuum is applied thereto for separating the alcohol-water from said first solvent and producing an alcohol-water first condensate, said first condensate constituting the phase delivered to said second solvent extraction column.

13. The process defined in claim 11 wherein an overhead containing alcohol is formed in the second vacuum stripper, the alcohol from the overhead of the second vacuum stripper being removed under vacuum, cooled and condensed, and then pumped to storage.

14. The process of claim 11 wherein two cycles are used to comprise a system enabling both high alcohol recovery through the recycle of a second raffinate to a first solvent extraction cycle and the production of a dry alcohol product through the processing of the first condensate in a second extraction cycle.

15. A process of extracting alcohol from a dilute aqueous mixture containing the alcohol comprising commingling the dilute aqueous mixture with a first organic solvent selected from the group consisting of n-paraffin, isoparaffin, long chain alcohols, long chain acetate esters, and long chain fatty acids which dissolve the alcohol and are essentially immiscible with water for providing a first extract and a first raffinate, producing said first extract from said first raffinate using a first extraction column, feeding said first extract to a first vacuum stripper and applying a vacuum thereto for separating the alcohol-water from said first solvent and producing an alcohol-water first condensate, drying said first condensate from first vacuum stripper by commingling said second condensate with a second organic solvent selected from the group consisting of n-paraffin, isoparaffin, long chain alcohols, long chain acetate esters, and long chain fatty acids, producing a second extract and a second raffinate using a second solvent extraction column and separating the alcohol from said second extract phase.

16. The process defined in claim 15 wherein said long chain alcohols include tridecyl alcohol and decyl alcohol.

17. The process defined in claim 15 wherein said long chain fatty acid ester includes coconut, tallow and linseed oil.

* * * * *